United States Patent
Nord et al.

(10) Patent No.: US 10,195,463 B2
(45) Date of Patent: Feb. 5, 2019

(54) METHOD AND APPARATUS PERTAINING TO THE USE OF IMAGING AND SURFACE INFORMATION TO INFLUENCE A RADIATION TREATMENT PLAN TO ACCOMMODATE DYNAMIC PHYSICAL CHANGES DURING THE TREATMENT

(75) Inventors: Janne Nord, Espoo (FI); Juha Kauppinen, Espoo (FI); Lauri Halko, Helsinki (FI)

(73) Assignee: Varian Medial Systems International AG, Steinhausen (CH)

( * ) Notice: Subject to any disclaimer, the term of this patent is extended or adjusted under 35 U.S.C. 154(b) by 532 days.

(21) Appl. No.: 12/784,805

(22) Filed: May 21, 2010

(65) Prior Publication Data

US 2011/0286642 A1 Nov. 24, 2011

(51) Int. Cl.
*G06K 9/00* (2006.01)
*A61N 5/10* (2006.01)

(52) U.S. Cl.
CPC ......... *A61N 5/1037* (2013.01); *A61N 5/1038* (2013.01); *A61N 2005/1059* (2013.01)

(58) Field of Classification Search
CPC .............................. A61N 5/1037; A61N 5/1038
USPC .......................................................... 382/128
See application file for complete search history.

(56) References Cited

U.S. PATENT DOCUMENTS

| | | | |
|---|---|---|---|
| 7,280,633 B2 * | 10/2007 | Cheng .................. | A61N 5/1067 378/117 |
| 7,348,970 B2 | 3/2008 | da Cunha et al. | |
| 7,348,974 B2 | 3/2008 | Smith et al. | |
| 8,063,376 B2 * | 11/2011 | Maniawski et al. ..... | 250/363.02 |
| 2008/0049896 A1 * | 2/2008 | Kuduvalli ............ | A61N 5/1049 378/65 |
| 2009/0052760 A1 | 2/2009 | Smith et al. | |
| 2011/0135190 A1 * | 6/2011 | Maad .......................... | 382/154 |

FOREIGN PATENT DOCUMENTS

| | | |
|---|---|---|
| GB | 2390792 B1 | 8/2005 |
| GB | 2407466 B1 | 1/2006 |

* cited by examiner

*Primary Examiner* — Hiep V Nguyen
(74) *Attorney, Agent, or Firm* — Fitch, Even, Tabin & Flannery LLP (57) ABSTRACT

A radiation-treatment planning apparatus accesses imaging information regarding at least a patient's treatment volume and surface information regarding dynamic surfaces within the radiation-treatment environment as pertains to the radiation treatment. The apparatus acquires the imaging information using a first imaging technology and the surface information using a second technology that is different than the first imaging technology. The apparatus uses the imaging and surface information to influence a radiation treatment plan for treating the treatment volume with radiation to accommodate dynamic physical changes within the radiation-treatment environment during the radiation treatment of the treatment volume.

17 Claims, 3 Drawing Sheets

METHOD AND APPARATUS PERTAINING TO THE USE OF IMAGING AND SURFACE INFORMATION TO INFLUENCE A RADIATION TREATMENT PLAN TO ACCOMMODATE DYNAMIC PHYSICAL CHANGES DURING THE TREATMENT

TECHNICAL FIELD

This invention relates generally to dynamic radiation treatment of treatment volumes.

BACKGROUND

The use of radiation (such as x-rays, protons, and so forth) to treat specific portions of the human body comprises a well-known area of endeavor. Generally speaking, such radiation serves to inhibit or destroy unwanted living material such as a tumor. Unfortunately, such radiation can be harmful to wanted portions of the patient's living material as well. Accordingly, treatment plans serve to control the radiation treatment process by attempting to maximize the therapeutic value of the radiation while minimizing collateral damage or risk.

It is known to modify a given treatment plan that extends over a given number of days or weeks (via a plurality of individual dosings) to accommodate certain dynamic physical changes that occur slowly over time. For example, the settings for a multi-leaf collimator may be altered to accommodate a change in the size of the treatment volume itself over time.

The applicant notes, however, that not all physical changes of relevance in a radiation-treatment setting occur slowly over time. In some cases, for example, real-time movements of the patient during the treatment process can materially impact the relative therapeutic value of the corresponding dosing. Depending upon the treatment plan, this can include both significant dynamic activity (as when the patient moves a limb) as well as relatively slight dynamic activity (as when the upper torso moves with the patient's breathing).

Other potentially relevant physical movement can derive from other objects in the radiation-treatment environment. In many cases, for example, the radiation source may move while administering radiation dosings. At the same time, or in lieu thereof, one or more patient support structures (such as all or portions of a couch) may move.

When such dynamic events occur during the treatment process the results can be undesirable. In some cases the movement can lead to physical conditions that vary so significantly from the assumptions of the treatment plan that attaining the desired therapeutic results becomes unlikely. In other cases the movement can lead to actual collisions between two or more structures in the radiation-treatment environment.

There are prior art approaches that seek to detect and accommodate in some fashion at least limited categories of such dynamic events. While perhaps successful for some limited purposes, the applicant has determined that there remains considerable room for improvement in these regards.

BRIEF DESCRIPTION OF THE DRAWINGS

The above needs are at least partially met through provision of the method and apparatus pertaining to the use of imaging and surface information to influence a radiation treatment plan to accommodate dynamic physical changes during the treatment described in the following detailed description, particularly when studied in conjunction with the drawings, wherein.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, pursuant to these various embodiments, a radiation-treatment planning apparatus accesses imaging information regarding at least a patient's treatment volume and surface information regarding dynamic surfaces within the radiation-treatment environment as pertains to the radiation treatment. The apparatus acquires the imaging information using a first imaging technology and the surface information using a second technology that is different than the first imaging technology. The apparatus uses the imaging and surface information to influence a radiation treatment plan for treating the treatment volume with radiation to accommodate dynamic physical changes within the radiation-treatment environment during the radiation treatment of the treatment volume.

By one approach, the second technology comprises a time-of-flight measurement technology. Such an approach can be deployed in a cost-effective manner and utilized in a real-time and non-invasive manner.

By one approach, the aforementioned use of the imaging and surface information serves to avoid contact between the dynamic components of the radiation-treatment apparatus and other surfaces within the radiation-treatment environment. These other surfaces can comprise, for example, patient surfaces, patient-fixation devices, patient-support structures, and so forth.

By one approach these approaches will accommodate using such information prior to treating the patient with the radiation treatment plan. By another approach, used in combination with the foregoing or in lieu thereof, these approaches will accommodate so using such information while actually treating the patient with the radiation treatment plan.

So configured, numerous potential benefits are attained. By approach, for example, collisions during the treatment can be avoided. These teachings can also help to ensure that the full therapeutic value of a given treatment plan remains realized, or that unwanted harm remains unrealized, by permitting real-time (or near real-time) responses to sudden unexpected movement of interest (such as movements of the patient themselves).

These teachings are readily utilized in conjunction with various existing devices and components. Accordingly, these teachings can serve to significantly leverage the capabilities and effectiveness of such platforms. These teachings are also highly scalable and can be employed in conjunction with a widely ranging number and kind of moving surfaces.

Figure 1:
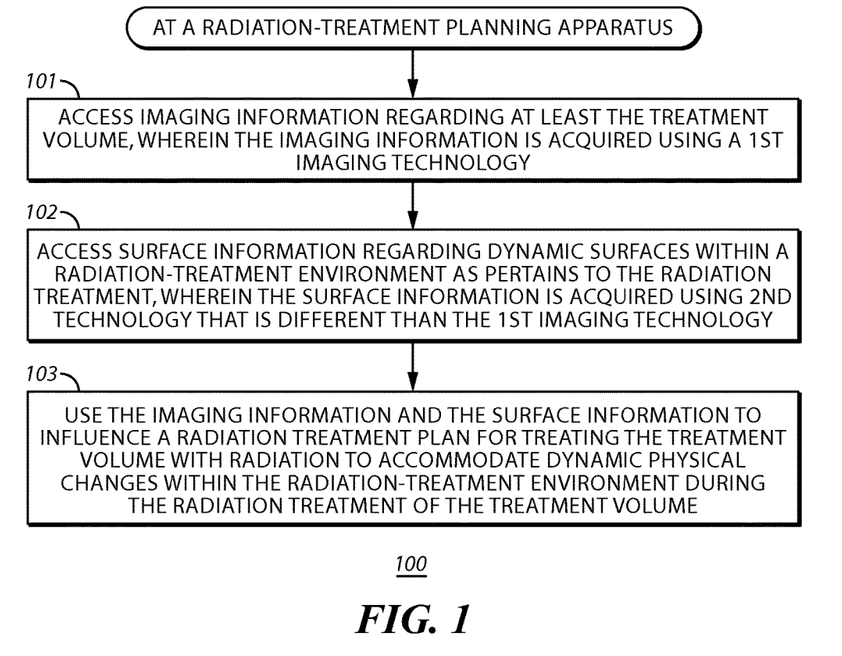
FIG. 1 comprises a flow diagram as configured in accordance with various embodiments of the invention.

These and other benefits may become clearer upon making a thorough review and study of the following detailed description. Referring now to the drawings, and in particular to FIG. 1, an illustrative process 100 that is compatible with many of these teachings will now be presented.

Figure 2:
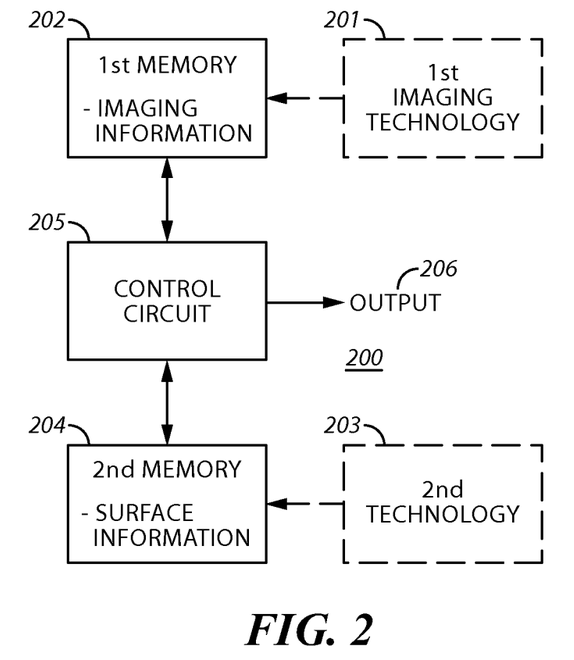
FIG. 2 comprises a block diagram as configured in accordance with various embodiments of the invention.

This process 100 can be carried out via a radiation-treatment planning apparatus. FIG. 2 presents an illustrative example in these regards. Depending upon the needs and/or opportunities as tend to characterize a given application setting, this radiation-treatment planning apparatus can be physically and logically separate from the radiation-treatment apparatus that will implement, in whole or in part, the corresponding treatment plan or can be, in whole or in part, physically and/or logically integral with the radiation-treatment apparatus.

In this non-limiting example, the radiation-treatment planning apparatus 200 includes a first memory 202 having imaging information stored therein. This imaging information pertains to the treatment volume of a given patient (such as, for example, a particular tumor located within the patient) and is initially acquired using a first imaging technology 201 of choice. By one approach, for example, this first imaging technology 201 can comprise computed tomography (CT) (including but not limited to two-dimensional, three-dimensional, or four-dimensional CT content). Numerous other imaging technologies may be considered in these same regards. These teachings will also accommodate fusing the content of differing imaging technologies that rely, for example, upon differing imaging modalities. Imaging technologies are well known in the art. Accordingly, for the sake of brevity, further elaboration will not be presented here in these regards.

This apparatus 200 also includes, in this illustrative example, a second memory 204. This second memory 204 stores surface information regarding one or more dynamic surfaces within the radiation-treatment environment as pertains to the radiation treatment. These can be essentially any surfaces that are present in such an operational context. Examples include, but are not limited to, patient surfaces, patient-support surfaces, patient-fixation surfaces, radiation-treatment surfaces (including but not limited to gantries, tracks, frames, radiation sources, shields, jaws and collimators (including multi-leaf collimators), attending technicians and/or other authorized (or unauthorized) persons, and so forth). (It will be understood that this "surface information" is not merely limited to a single point and/or a single corresponding linear distance.)

A second technology 203 serves to acquire this surface information. This second technology is "second" in that it is different than the first imaging technology in a given instantiation. Examples include, but are not limited to, one or more single-frame visual image-capture-based platforms (such as digital cameras), one or more multi-frame (such as video) visual image-capture-based platforms (such as digital video cameras), and the like.

By one approach, this second technology comprises a time-of-flight measurement technology. There are various time-of-flight-based cameras known in the art, for example. Such cameras often combine a pulsed laser with a custom imaging integrated circuit. Such a camera also often serves to provide a fast counter behind every pixel. So configured, such a device can produce depth values for each pixel in a given frame. This information, in turn, can readily serve to provide a depth-based view of a given physical surface.

As noted above, time-of-flight methodologies are known in the art though such approaches have not been previously used for the purposes described here. Notwithstanding the apparent reticence of past practitioners to consider use of a time-of-flight measurement approach for purposes such as these, the applicant's have determined that a time-of-flight-based approach can prove particularly effective in many application settings.

Generally speaking, time-of-flight measurements directly pertain to the three-dimensional spatial features of the surfaces being measured. This, in turn, can simplify the computational requirements to make the kinds of usage described herein. The applicant has also discovered that reconstruction of useful surface information using time-of-flight measurement technologies can also avoid the need for multiple image-capture points of view as typically characterizes a visual camera-based approach and/or the need for time-consuming scanning processes.

The applicant has identified other benefits that arise when using of a time-of-flight measurement approach as compared to a multi-camera approach. As one example in these regards, the applicants have determined that constructing a three-dimensional interpretation of the inherently two-dimensional results provided by each camera requires considerable time and/or computational capability, or a willingness to accept a degree of error that the applicants find undesirable.

The applicants have also determined, as another example, that a camera-based approach can yield questionable results when the movable surface of interest are similarly colored and/or illuminated. Unfortunately, it is not unusual for a typical radiation-treatment environment to be well (and relatively uniformly) illuminated and/or for many of its constituent surfaces to be similarly (or even exactly) colored. One often-important surface in these regards is the skin of the patient themselves. Unfortunately, human skin often presents a relatively evenly and uniformly colored surface and the applicant has determined that this, too, can undercut the effectiveness of camera-based solutions.

As yet another relevant observation in these same regards, the applicants have determined that such cameras, when employed for such purposes, can be challenging to accurately and persistently maintain with respect to a specific position, angle, and/or field of view over what can be a relatively long period of time as corresponds to a given radiation-treatment dosing and/or treatment plan.

Accordingly, while the present teachings can be successfully used in at least some application settings in conjunction with ordinary digital cameras, in many operational paradigms a time-of-flight measurement approach can serve in a particularly beneficial manner and may be preferred in such settings. As but one illustrative example in these regards, consider that protons having a certain energy travel only a certain distance in a given material. It is therefore important to have correct information about the amount of material in the proton's path to the intended stopping location. Proton treatment platforms, however, generally do not have integrated three-dimensional imaging capability. Per the present teachings a time-of-flight camera can be readily added to the proton-treatment environment to image the relevant surface shapes. Energy and other proton delivery parameters can then be adjusted based on this surface information (in real time, if desired) to effect the desired dosing.

In any event, these teachings will accommodate acquiring and accessing some or all of this surface information well prior to administering the corresponding treatment plan for the purposes described herein and/or acquiring and/or accessing some or all of this surface information during administration of the treatment plan. This, in turn, will permit, if desired, using a first imaging technology to facilitate modeling delivery of the doses in order to avoid collisions during delivery and then using that same first imaging technology or a second, different imaging technology to image the dynamic surfaces of interest (continuously or discontinuously as desired or appropriate) during the course of administering the treatment plan.

This first and second memory 202 and 204 can comprise, if desired, discrete physical components as suggested by FIG. 2. This illustration can also be viewed as a logical (as versus a physical) presentation in these regards, however, such that these two memories can be served by a single physical device. These teachings will also readily accommodate using a plurality of physical memory devices or components to serve as one of these first and second memories 202 and 204. It will also be understood that one of both of these memories can be local or can be remotely located (such as in a different building, facility, state or territory, country, or continent). Such architectural options are well understood in the art and require no further elaboration here.

The aforementioned control circuit 205 operably couples to the first and second memories 202 and 204 and therefore has access to the relevant imagining information and the surface information as pertains to a given application setting. This control circuit 205 is configured (using, for example, programming as will be well understood by those skilled in the art) to then carry out one or more of the steps, actions, and/or functions described herein as desired. Such a control circuit can comprise a fixed-purpose hard-wired platform or can comprise a partially or wholly programmable platform. These architectural options are well known and understood in the art and require no further description here.

Such an apparatus 200 may be comprised of a plurality of physically distinct elements as is suggested by the illustration shown in FIG. 2. It is also possible, however, to view this illustration as comprising a logical view, in which case one or more of these elements can be enabled and realized via a shared platform. It will also be understood that such a shared platform may comprise a wholly or at least partially programmable platform as are known in the art.

Referring again to FIG. 1, this process 100 provides the step 101 of accessing the aforementioned imaging information regarding at least a given patient's treatment volume. Similarly, step 102 provides for accessing surface information regarding dynamic surfaces within the relevant radiation-treatment environment as pertains to the radiation treatment.

In some cases, some of this surface information can comprise previously-acquired information. This can be appropriate where the surfaces in question tend to remain constant and static over long periods of time and hence are not likely to move from the location denoted in such information.

In many cases, however, this surface information will be acquired either immediately before the radiation treatment (such as, for example, within 10 minutes of the start of such a treatment, or within one hour of the start of such a treatment, to note but two examples in this regard) and/or during the actual course of the radiation treatment (which can include during the administration of radiation doses and/or during intervals between such dosings).

Figure 3:
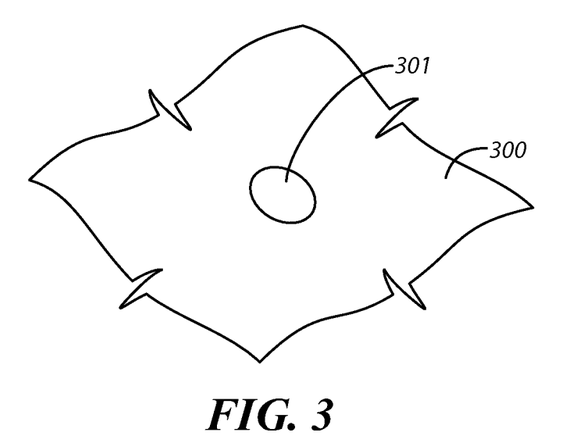
FIG. 3 comprises a perspective detail view as configured in accordance with various embodiments of the invention.

In many cases a dynamic surface of interest will comprise at least a given portion of the patient's skin. This can relate, for example, to when a patient inhales, exhales, or moves, for example, a particular limb. In some cases (for example, when using ordinary digital cameras (either in combination with time-of-flight approaches or in lieu thereof)) it may be useful to apply one or more targets to a patient's skin to render it easier to more accurately detect such movement. As shown in FIG. 3, such a target 301 can comprise a disc-shaped object (such as a plastic or metal disc) that can be temporarily adhered to the patient 300 using an appropriate adhesive. This target 301, owing to its color, shape, and/or constituent materials may be easier to identify and hence easier to track for the purposes of making movement-detection comparisons.

By one approach, this surface information can serve to completely describe and characterize the entire treatment environment. In many cases, however, such completeness is unnecessary. It may not be helpful, for example, to know where the walls of the treatment environment are located. Generally speaking, it is the dynamic surfaces (i.e., the surfaces that can and will tend to move between radiation treatments and/or during the course of a given treatment) that tend to be of greatest interest for the present purposes.

Depending upon the application setting, it may not be useful or necessary to access information regarding literally all dynamic surfaces within such an operating environment. Instead, this step 102 can pertain to accessing information regarding some selected subset of all candidate dynamic surfaces. The criteria to define this subset can vary, of course, with the needs and/or opportunities that tend to characterize a given application setting.

Figure 4:
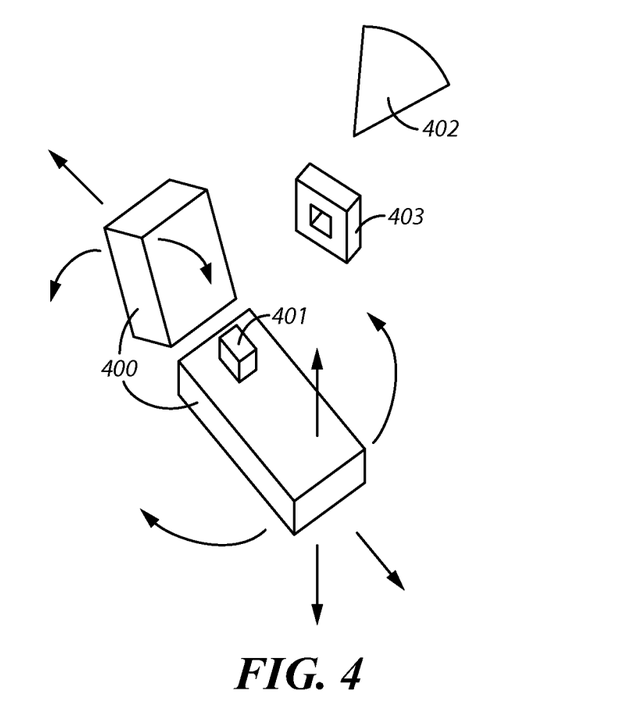
FIG. 4 comprises a perspective schematic view as configured in accordance with various embodiments of the invention.

FIG. 4 provides a schematic view of a number of candidate dynamic surfaces of possible interest in these regards. A patient support surface (such as a couch) 400 that is itself capable of movement can be of particular interest. This can include a horizontal portion that can move, for example, up and down, to and fro, and/or about one or more pivot points. This can also include a back-support surface that may move in these same regards but that also may be capable of further relative motion with respect to the aforementioned horizontal portion.

One or more patient fixation mechanisms 401 that are present in a given treatment setting can also be of interest. The presence, nature, location, and orientation of such fixation mechanism can vary greatly from one treatment plan to another, and even from one dosing to another in accordance with a same treatment plan.

In many application settings the radiation source 402 can move. This can be accompanied by movement of a variety of corresponding members, components, and structures such as gantries, chains, belts, arms, and so forth. Similarly, one or more collimators and/or jaws 403 as present in a given treatment setting can often move.

It will be understood that the foregoing examples are intended to serve an illustrative purpose and are not intended to comprise an exhaustive listing of all dynamic surface of potential interest in all possible application settings.

Referring again to FIG. 1, this process 100 then provides the step 103 of using the imaging information and the surface information to influence a radiation treatment plan for treating the treatment volume with radiation to accommodate dynamic physical changes within the radiation-treatment environment during the radiation treatment of the treatment volume.

By one approach, this can comprise using the information in this manner prior to treatment the patient with the radiation treatment plan. For example, by comparing the instructions of the treatment plan and the corresponding location of various surfaces as will result from compliance with such instructions with the actual present location of such surfaces, a determination can be made regarding the likelihood that such a plan can be presently carried out without an undue risk of collision between two or more of these surfaces.

By another approach, alone or in combination with the foregoing, this use of the information can occur while treating the patient with the radiation treatment plan. Such an approach can serve to take into account dynamic movements that have occurred subsequent to initiation of the treatment plan and which now give rise to an increased risk of, for example, an unwanted collision.

As already alluded to above, this step 103 can comprise using this information to avoid contact between dynamic components of a corresponding radiation-treatment apparatus and other surfaces (such as patient surfaces, patient-support surfaces, patient-fixation surfaces, and so forth) within the radiation-treatment environment. These teachings will readily serve to facilitate other purposes as well, however.

For example, by one approach, this step 103 can comprise dynamically modifying the radiation treatment to accommodate physical movement of the patient during the radiation treatment. As one illustrative non-limiting example in these regards, and referring momentarily to FIG. 5, this can comprise halting the treatment in response to detecting that the patient 300 has moved a target area (such as their arm 500) to such an extent 501 that at least some portion of the patient is now beyond a permitted range of movement as corresponds to the purposes of the treatment.

Figure 5:
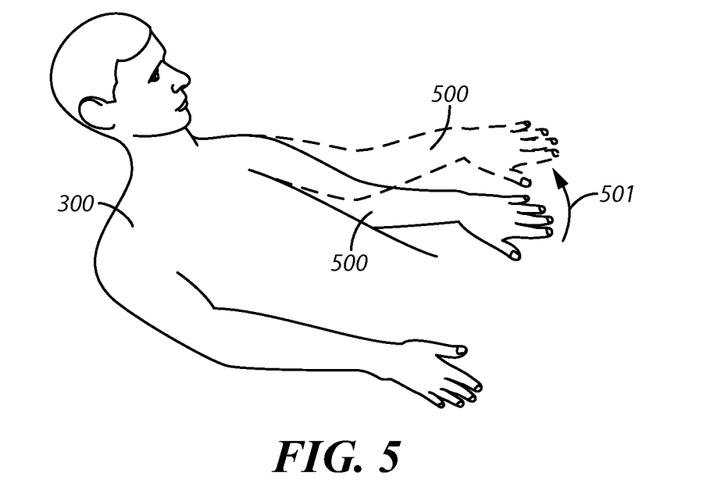
FIG. 5 comprises a perspective schematic view as configured in accordance with various embodiments of the invention.

As another illustrative non-limiting example in these regards, this can comprise modifying treatment parameters (such as beam "on" time and/or beam intensity) in response to such things as physical movement due to the patient's breathing.

These teachings comprise a highly flexible approach that can be readily leveraged in various ways. As one illustrative example in these regards, the aforementioned usage can comprise comparing the imaging information with previous imaging information (for this same patient) to determine a change regarding the location of a given patient surface and causing the radiation treatment plan to account for that change. This approach will permit, for example, readily determining patient weight gain or weight loss (as compared to a previous treatment plan consideration) and then accounting for that change with respect to the treatment plan (for example, by modifying the pulse to ensure accurate administration of a desired dosage).

As another illustrative example in these regards, the aforementioned usage can comprise, if desired, accommodating dynamic physical changes within the radiation-treatment environment during the radiation treatment of the treatment volume by causing selective movement of a dynamic surface other than a patient-support surface. This can comprise, for example, causing movement of a collimator and/or jaw, or some part of the radiation delivery platform itself. This change can be occasioned to avoid anticipated or impending collisions. Such a change can also be occasioned to accommodate the newly-introduced usage of a particular patient-fixation mechanism or physical changes as pertain to the patient themselves.

As yet another illustrative example in these regards, patient surface information can be acquired continuously during patient set up (that is, during the preparative steps that often occur before dose delivery can be started). By comparing this real-time information with previously acquired and stored similar information, these teachings can be applied to guide users to set up the patient correctly and help in reproducing the patient set up in different fractions of treatment dose delivery. As one illustrative use case in these regards, an end-user display (using, for example, multiple displays or a split-screen approach) can depict both current patient surface information along with stored reference surface information to enable visual comparisons to inform the making of adjustments to the current patient set up. As another illustrative use case in these regards, these teachings will accommodate projecting visual information regarding how to adjust the set up at a given point of time based on, for example, an algorithmic evaluation of both current surface information and stored reference surface information.

Accordingly, it will be well understood by those skilled in the art that these teachings, though economically deployable and highly scalable over a wide variety of technologies and application settings, comprise a highly flexible and powerful mechanism to accommodate the dynamic realties of patients and radiation-treatment paradigms.

Those skilled in the art will recognize that a wide variety of modifications, alterations, and combinations can be made with respect to the above described embodiments without departing from the spirit and scope of the invention, and that such modifications, alterations, and combinations are to be viewed as being within the ambit of the inventive concept.

We claim:

1. A method for use with dynamic radiation treatment of a treatment volume that comprises a part of a patient, the method comprising:
   at a radiation-treatment planning apparatus:
      accessing imaging information regarding at least the treatment volume, wherein the imaging information is acquired using a first imaging technology;
      accessing surface information regarding dynamic surfaces within a radiation-treatment environment as pertains to the radiation treatment, wherein the surface information is acquired using a second technology that is different than the first imaging technology and wherein the dynamic surfaces comprise non-patient surfaces comprising at least one of a patient-support surface, a patient-fixation surface, a radiation-treatment gantry, a radiation-treatment track, a radiation-treatment frame, a radiation-treatment radiation source, a radiation-treatment jaw, and a radiation-treatment collimator;
      using the imaging information and the surface information to influence a radiation-treatment plan for treating the treatment volume with radiation by modifying the radiation-treatment plan while treating the patient with the radiation-treatment plan to avoid collisions amongst the dynamic surfaces within the radiation-treatment environment.

2. The method of claim 1 wherein the first imaging technology comprises computed tomography.

3. The method of claim 1 wherein the second technology comprises a time-of-flight measurement technology.

4. The method of claim 1 wherein influencing the radiation-treatment plan comprises calculating the radiation-treatment plan prior to treating the patient with the radiation-treatment plan.

5. The method of claim 1 wherein accessing surface information regarding dynamic surfaces comprises imaging the dynamic surfaces while treating the patient with the radiation-treatment plan.

6. The method of claim 1 wherein modifying the radiation treatment comprises halting the radiation treatment.

7. The method of claim 1 wherein using the imaging information and the surface information to influence a radiation-treatment plan for treating the treatment volume with radiation to avoid collisions amongst the dynamic surfaces within the radiation-treatment environment comprises comparing information regarding expected movement of the target against tracked movement of the target.

8. A method for use with dynamic radiation treatment of a treatment volume that comprises a part of a patient, the method comprising:
at a radiation-treatment planning apparatus:
accessing imaging information regarding at least the treatment volume, wherein the imaging information is acquired using a first imaging technology;
accessing surface information regarding dynamic surfaces within a radiation-treatment environment as pertains to the radiation treatment, wherein the surface information is acquired using a second technology that is different than the first imaging technology and that comprises a time-of-flight measurement technology and wherein the dynamic surfaces comprise non-patient surfaces comprising at least one of a patient-support surface, a patient-fixation surface, a radiation-treatment gantry, a radiation-treatment track, a radiation-treatment frame, a radiation-treatment radiation source, a radiation-treatment jaw, and a radiation-treatment collimator;
using the imaging information and the surface information to influence a radiation-treatment plan for treating the treatment volume with radiation by modifying the radiation-treatment plan while treating the patient with the radiation-treatment plan to accommodate dynamic physical changes within the radiation-treatment environment during the radiation treatment of the treatment volume to avoid collisions amongst the dynamic surfaces within the radiation-treatment environment.

9. The method of claim 8 wherein the first imaging technology comprises computed tomography.

10. The method of claim 8 wherein using the imaging information and the surface information to influence a radiation-treatment plan for treating the treatment volume with radiation comprises, at least in part, dynamically modifying the radiation treatment to accommodate physical movement of the patient during the radiation treatment.

11. The method of claim 10 wherein dynamically modifying the radiation treatment comprises halting the radiation treatment.

12. The method of claim 8 wherein using the imaging information and the surface information to influence a radiation-treatment plan for treating the treatment volume with radiation to accommodate the dynamic physical changes within the radiation-treatment environment during the radiation treatment of the treatment volume comprises using the surface information to prospectively determine whether a suitable radiation treatment can be presently effected with the patient in view of monitored movement of the dynamic surfaces.

13. A method for use with dynamic radiation treatment of a treatment volume that comprises a part of a patient, the method comprising:
at a radiation-treatment planning apparatus:
accessing imaging information regarding at least the treatment volume, wherein the imaging information is acquired using a first imaging technology;
accessing surface information regarding dynamic surfaces within a radiation-treatment environment as pertains to the radiation treatment, wherein the surface information is acquired using a second technology that is different than the first imaging technology and wherein the dynamic surfaces comprise non-patient surfaces comprising at least one of a patient-support surface, a patient-fixation surface, a radiation-treatment gantry, a radiation-treatment track, a radiation-treatment frame, a radiation-treatment radiation source, a radiation-treatment jaw, and a radiation-treatment collimator;
using the imaging information and the surface information to influence a radiation-treatment plan for treating the treatment volume with radiation by modifying the radiation-treatment plan while treating the patient with the radiation-treatment plan to accommodate dynamic physical changes amongst the dynamic surfaces within the radiation-treatment environment during the radiation treatment of the treatment volume by causing selective movement of at least one of the dynamic surfaces other than a patient-support surface to avoid collisions amongst the dynamic surfaces within the radiation-treatment environment.

14. The method of claim 13 wherein the second technology comprises a time-of-flight measurement technology.

15. The method of claim 13 wherein the dynamic surface comprises a surface comprising a part of a radiation delivery platform.

16. A radiation-treatment planning apparatus configured to develop a treatment plan to provide dynamic radiation treatment of a treatment volume that comprises a part of a patient, the apparatus comprising:
a first memory having imaging information regarding the treatment volume stored therein, wherein the imaging information is acquired using a first imaging technology;
a second memory having surface information regarding dynamic surfaces within a radiation-treatment environment as pertains to the radiation treatment stored therein, wherein the surface information is acquired using a second technology that is different than the first imaging technology and wherein the dynamic surfaces comprise non-patient surface comprising at least one of a patient-support surface, a patient-fixation surface, a radiation-treatment gantry, a radiation-treatment track, a radiation-treatment frame, a radiation-treatment radiation source, a radiation-treatment jaw, and a radiation-treatment collimator;
a control circuit operably coupled to the first and second memory and configured to use the imaging information and the surface information to influence a radiation-treatment plan for treating the treatment volume with radiation by modifying the radiation-treatment plan while treating the patient with the radiation-treatment plan to avoid collisions amongst the dynamic surfaces within the radiation-treatment environment.

17. A radiation-treatment planning apparatus configured to develop a treatment plan to provide dynamic radiation treatment of a treatment volume that comprises a part of a patient, the apparatus comprising:
- a first memory having imaging information regarding at least the treatment volume stored therein, wherein the imaging information is acquired using a first imaging technology;
- a second memory having surface information regarding dynamic surfaces within a radiation-treatment environment as pertains to the radiation treatment stored therein, wherein the surface information is acquired using a second technology that is different than the first imaging technology and that comprises a time-of-flight measurement technology and wherein the dynamic surfaces comprise non-patient surfaces comprising at least one of a patient-support surface, a patient-fixation surface, a radiation-treatment gantry, a radiation-treatment track, a radiation-treatment frame, a radiation-treatment radiation source, a radiation-treatment jaw, and a radiation-treatment collimator;
- a control circuit operably coupled to the first and second memory and configured to use the imaging information and the surface information to influence a radiation-treatment plan for treating the treatment volume with radiation by modifying the radiation-treatment plan while treating the patient with the radiation-treatment plan to accommodate dynamic physical changes within the radiation-treatment environment during the radiation treatment of the treatment volume to avoid collisions amongst the dynamic surfaces within the radiation-treatment environment.

* * * * *

UNITED STATES PATENT AND TRADEMARK OFFICE
CERTIFICATE OF CORRECTION

PATENT NO. : 10,195,463 B2  
APPLICATION NO. : 12/784805  
DATED : February 5, 2019  
INVENTOR(S) : Janne Nord, Juha Kauppinen and Lauri Halko

Page 1 of 1

It is certified that error appears in the above-identified patent and that said Letters Patent is hereby corrected as shown below:

On the Title Page

Item (73), Line 1, delete "Medial" and insert --Medical--.

Signed and Sealed this  
Twenty-sixth Day of November, 2019

Andrei Iancu  
*Director of the United States Patent and Trademark Office*